(12) United States Patent
Pheil et al.

(10) Patent No.: US 11,937,819 B2
(45) Date of Patent: Mar. 26, 2024

(54) STAPLE INSTRUMENT

(71) Applicant: Medline Industries, LP, Northfield, IL (US)

(72) Inventors: Natan Pheil, Highland Park, IL (US); Dinesh Koka, Winter Park, FL (US); Samuel Nader, Arlington Heights, IL (US); Wesley Reed, Libertyville, IL (US)

(73) Assignee: Medline Industries, LP, Northfield, IL (US)

( * ) Notice: Subject to any disclaimer, the term of this patent is extended or adjusted under 35 U.S.C. 154(b) by 0 days.

(21) Appl. No.: 17/899,067

(22) Filed: Aug. 30, 2022

(65) Prior Publication Data
US 2024/0065692 A1 Feb. 29, 2024

(51) Int. Cl.
*A61B 17/10* (2006.01)
(52) U.S. Cl.
CPC .................................. *A61B 17/10* (2013.01)
(58) Field of Classification Search
CPC . A61B 17/8872; A61B 17/0642; A61B 17/66; A61B 2017/081; Y10S 411/92
See application file for complete search history.

(56) References Cited

U.S. PATENT DOCUMENTS

| | | |
|---|---|---|
| 3,960,147 A * | 6/1976 | Murray ............... A61B 17/8872 606/101 |
| D337,159 S | 7/1993 | Hunt |
| 6,089,435 A | 7/2000 | Malek |
| 8,137,351 B2 | 3/2012 | Prandi |
| 8,382,767 B2 * | 2/2013 | Wassinger ............ A61F 2/4611 606/86 A |
| 9,095,338 B2 | 8/2015 | Taylor |
| 9,855,036 B2 | 1/2018 | Palmer |
| 9,861,413 B2 | 1/2018 | Palmer et al. |
| 10,064,619 B2 | 9/2018 | Palmer |
| 10,130,358 B2 | 11/2018 | Palmer |
| 10,610,218 B2 | 4/2020 | Palmer et al. |
| 10,945,725 B2 | 3/2021 | Hollis |

(Continued)

FOREIGN PATENT DOCUMENTS

EP 3563776 11/2019

OTHER PUBLICATIONS

Arthrex, Inc. Dynanite Product Technique and Highlights Brochure, 2019.

(Continued)

*Primary Examiner* — Nathaniel C Chukwurah
(74) *Attorney, Agent, or Firm* — Fitch, Even, Tabin & Flannery LLP

(57) ABSTRACT

A staple instrument is provided. The staple instrument includes a staple holder, a rotational drive shaft, and a linkage operatively coupled to the staple holder. The linkage is configured to expand the staple holder via an expansion motion imparted thereon. A converter coupling intermediate the rotational drive shaft and the linkage converts rotational motion of the rotational drive shaft into expansion of the staple holder. The staple instrument also includes a housing that supports the linkage, converter coupling, and rotational drive shaft. The rotational drive shaft has a stop surface that engages a corresponding surface formed in the housing to inhibit proximal translation of the rotational drive shaft relative to the housing.

20 Claims, 19 Drawing Sheets

(56) References Cited

U.S. PATENT DOCUMENTS

| | | | |
|---|---|---|---|
| 11,284,887 | B2 | 3/2022 | Hartdegen |
| D977,640 | S | 2/2023 | Ritz |
| 11,596,398 | B2 | 3/2023 | Wahl |
| 2016/0199060 | A1* | 7/2016 | Morgan ............... A61B 17/10 227/175.1 |
| 2017/0296174 | A1* | 10/2017 | Wahl ................... A61B 17/068 |
| 2018/0271521 | A1 | 9/2018 | Wahl |
| 2018/0317906 | A1 | 11/2018 | Hollis et al. |
| 2018/0344316 | A1 | 12/2018 | Palmer |
| 2022/0361877 | A1 | 11/2022 | Reed |
| 2023/0027093 | A1 | 1/2023 | Wahl |
| 2023/0200809 | A1 | 6/2023 | Wahl |

OTHER PUBLICATIONS

CrossRoads® Extremity Systems, LLC Announces Launch of the DynaFORCE™ Dynamic Compression Fixation System, https://www.crextremity.com/crossroads-extremity-systems-llc-announces-launch-of-the-dynaforce-dynamic-compression-fixation-system/, dated Jul. 11, 2017.

DePuy Synthes, BME Elite Implant Technique Overview, 2017.

DePuy Synthes, Speed Memory Implant Brochure, 2016-2018.

Medshape, Inc., Dynaclip Fixation System, Surgical Technique Guide, 2019.

NeoSpan Food, In2Bones, https://web.archive.org/web/20170410093305/http://i2b-USA.com/neospan-foot/, 2017.

NeoSpan SE Compression Staples, https://i2b-usa.com/neospan-se-compression-staple/, 2021.

Paragon 28, Inc., Surgical Technique Guide: JAWS Nitinol Staple System Brochure, 2020.

Stryker Corporation, "EasyClip Osteosynthesis Compression Staples," 2012.

Stryker Corporation, "EasyClip Osteosynthesis Compression Staples," 2015.

U.S. Food & Drug Administration, 510(k) Premarket Notification, https://www.accessdata.fda.gov/scripts/cdrh/cfdocs/cfpmn/pmn.cfm?ID=K161426, Oct. 24, 2016.

* cited by examiner

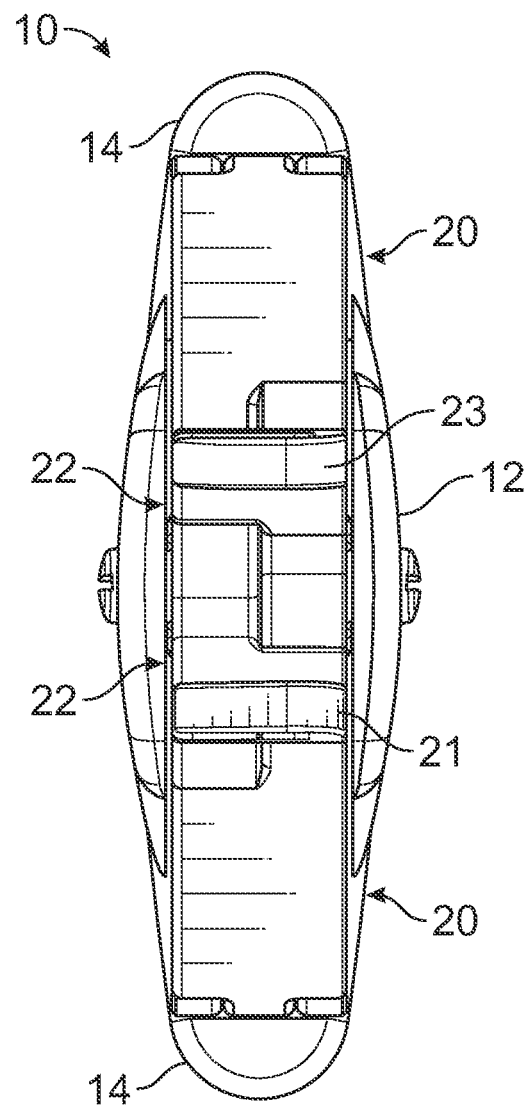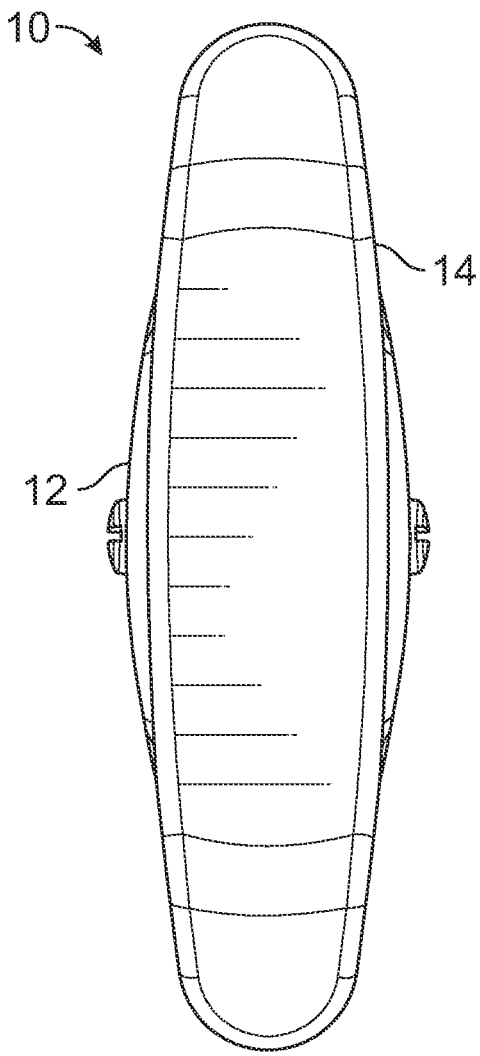
FIG. 6
FIG. 7

STAPLE INSTRUMENT

FIELD

The disclosure relates to medical instruments and, more particularly, to a medical instrument for inserting, removing and adjusting bone staples.

BACKGROUND

Surgical procedures such as fracture repairs, fusions, or osteotomies require bone tissue to form between bone segments. The ability for successful bone tissue growth at the site of the bone segments is improved when the bone segments are under compression. If there is no compression, a gap may form between the bone segments. These gaps tend to lengthen the healing time or impede complete healing. One method to achieve compression is the use of compression staples.

Compression staples include two or more legs interconnected by a bridge. These staples are commonly made from shape memory material, such as a nitinol alloy. When the legs of the staple are splayed, the shape memory material tends to bias the legs towards their initial resting positions, thereby causing the legs to exert an inward compressive force on bone or bone segments.

The splaying of the legs of the staple for insertion or adjustment can result in a large rebounding force. As such, there is a desire for an instrument that can open staples for use and that can reliably and repeatedly withstand the large rebounding forces generated during use of a staple instrument. One such instrument is described in U.S. patent application Ser. No. 17/322,580, assigned to Medline Industries, LP and entitled "Staple Instrument," which application is hereby incorporated by reference in its entirety. It is now desired to provide another such instrument.

BRIEF DESCRIPTION OF THE DRAWINGS

FIG. 6 is a bottom plan of the staple instrument of FIG. 1;

FIG. 7 is a top plan of the staple instrument of FIG. 1;

Figure 23:
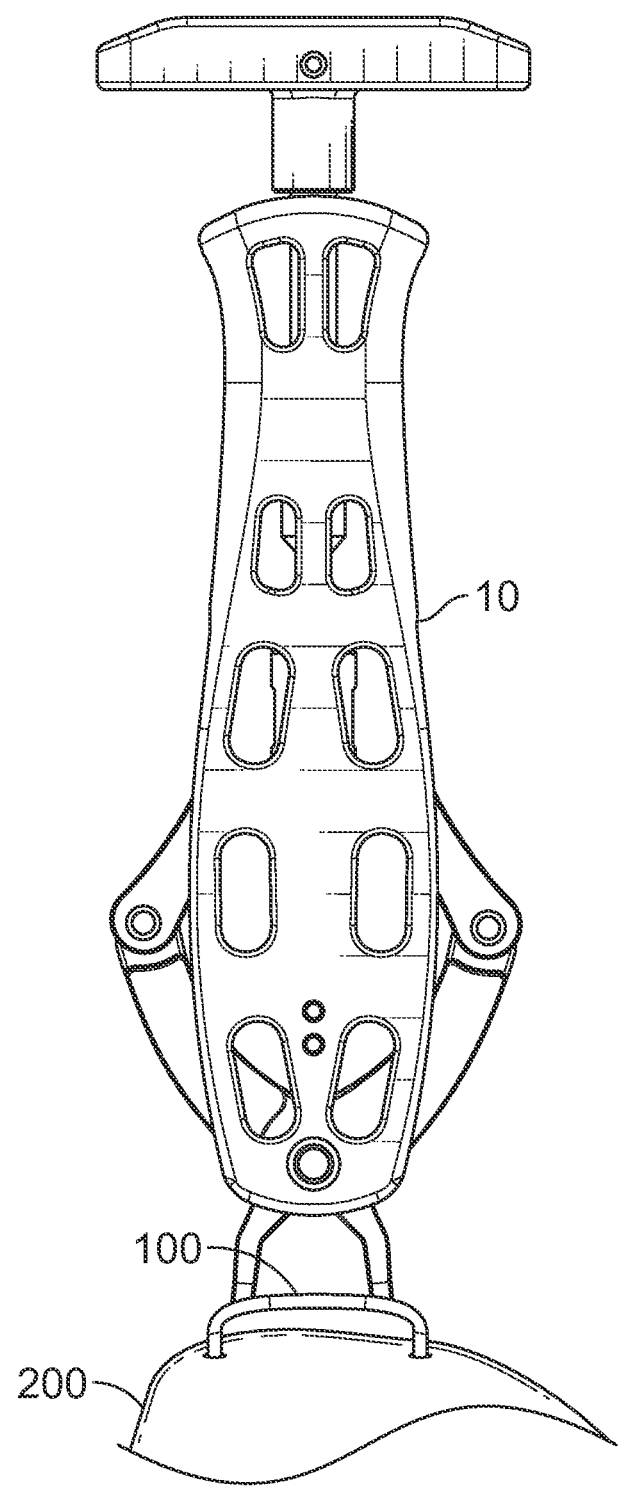
FIG. 23 is a front elevation of the staple instrument of FIG. 1 and a surgical staple, shown in the process of inserting the staple into a bone of a patient.

Terms of orientation are for convenient reference to the Figures and in particular the orientation of the staple instrument in FIG. 23. In practice, the device is omnidirectional and may be oriented in other positions.

DETAILED DESCRIPTION

With reference to FIGS. 1-7, the illustrated staple instrument 10 includes a housing 12, a rotational drive shaft 16 terminating in a handle 14, a converter coupling 18, a linkage 20, and a staple holder 22. The rotational drive shaft 16 is operatively coupled to the linkage 20 via the converter coupling 18, which, in some embodiments, can comprise a nut. The converter coupling 18 is intermediate of the rotational drive shaft 16 and the linkage 20. As will be explained hereinbelow in more detail, the housing 12 supports the linkage 20, the converter coupling 18, and the rotational drive shaft 16.

The staple instrument 10 is made from material that may be subjected to conventional cleaning and sterilization methods, such as steam, gas, and radiation sterilization methods. In the illustrated embodiment, the housing 12 is from a titanium alloy and the other components may be made from stainless steel. Other materials of construction are possible. These component parts may be manufactured via any suitable technique, such as stamping, milling, or additive manufacturing.

The staple holder 22 is in the form of discrete staple-engaging jaws 21, 23, and the linkage 20 is configured to separate the jaws 21, 23 via an expansion motion. The converter coupling 18 is configured to convert rotational motion of the rotational drive shaft 16 into the expansion motion of the staple holder 22, as explained in more detail below. The rotation of the rotational drive shaft 16 can be imparted by either manual and/or mechanical processes and, in some embodiments, can be effectuated by the handle 14. For example, when the handle 14 is rotated in a first direction, the rotational drive shaft 16 drives the converter coupling 18 away from the handle 14, which causes the linkage 20 to articulate in a manner that imparts the expansion motion to the staple holder 22 thereby separating the jaws 21, 23. The handle of the illustrated staple instrument 10 may be rotated in an opposing second direction to reverse the articulating movement of the linkage 20 to thereby cause the jaws 21, 23 to contract for removal of a staple from the staple instrument 10 or to permit reuse by permitting a new staple to be loaded onto the staple instrument 10.

Figure 8:
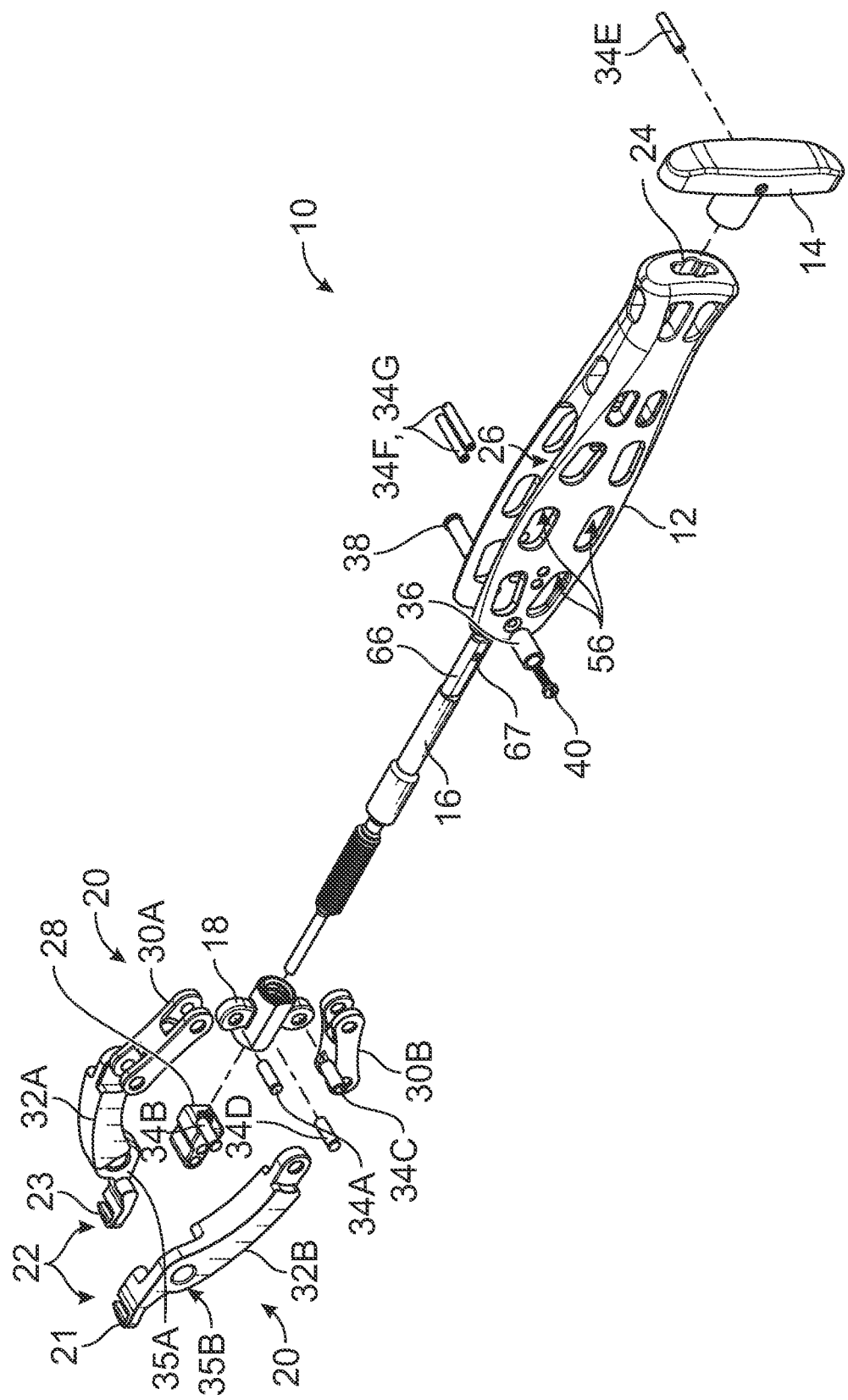
FIG. 8 is an exploded view of the staple instrument of FIG. 1.
Figure 16:
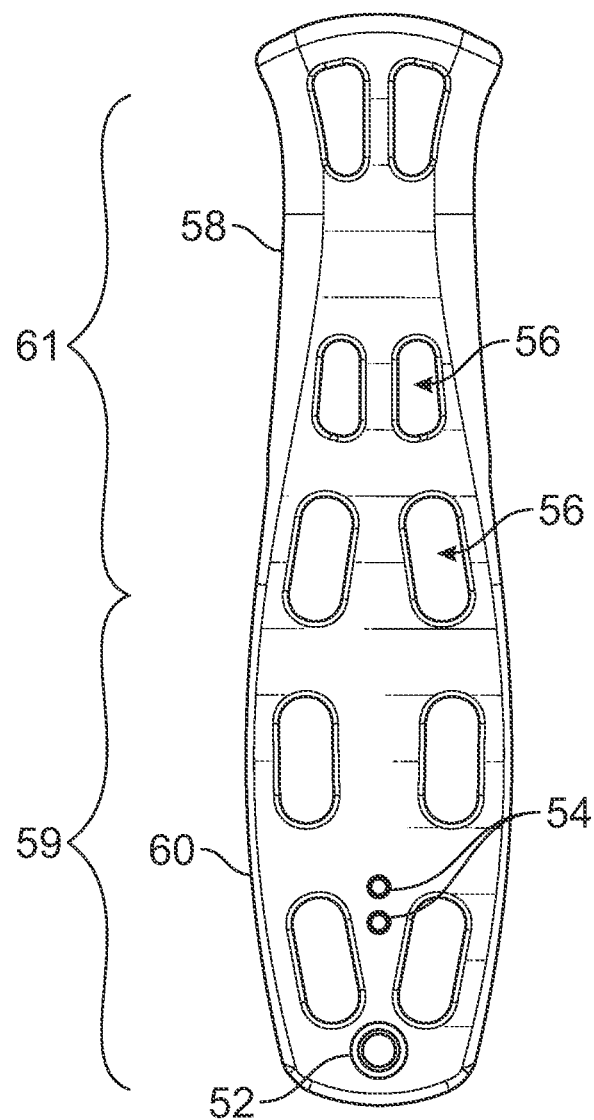
FIG. 16 is front elevation of the housing of the staple instrument of FIG. 1.
Figure 17:
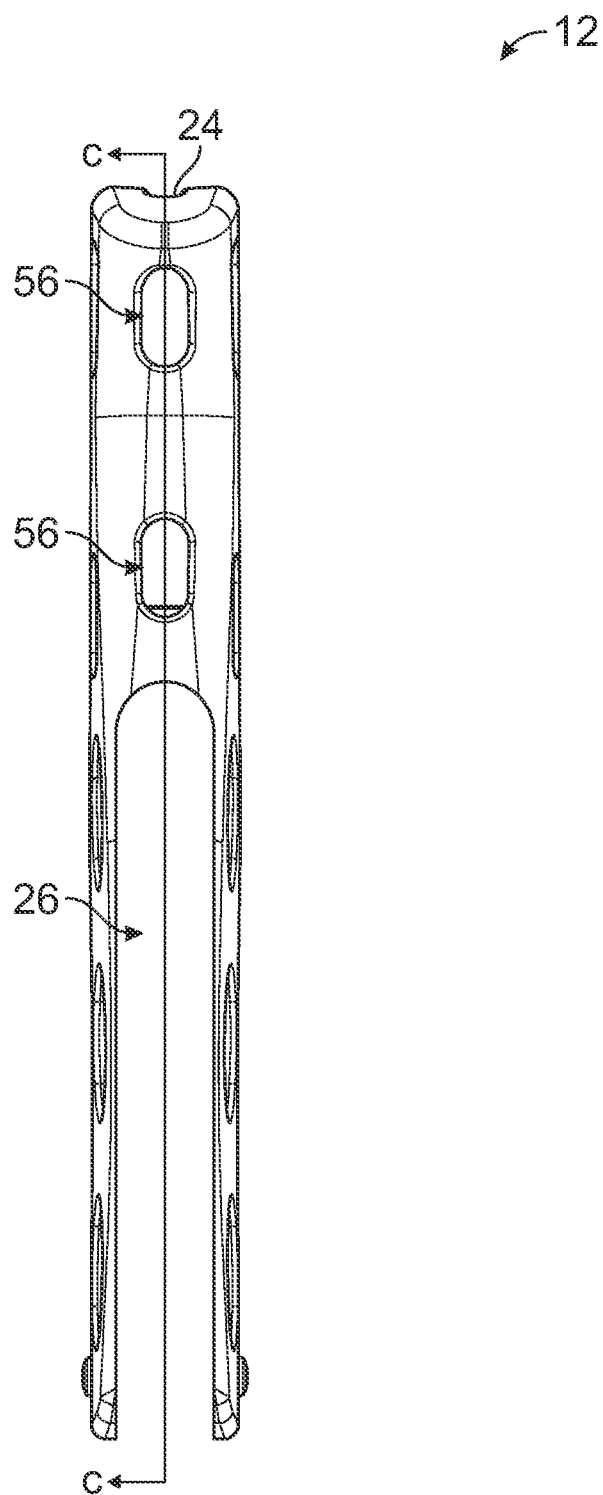
FIG. 17 is a left side elevation of the housing of the staple instrument of FIG. 1.

As seen in FIG. 8, the staple instrument 10 is composes of several component parts supported by the housing 12. The illustrated housing 12 is a monolithic one-piece structure but in alternative embodiments may be of a two-piece construction where fasteners or coupling surfaces are used to hold the housing 12 together. The profile of the housing 12 is designed to conform ergonomically to a user's hand, and has a relatively long convex portion 60 along a distal profile region 59 and a relatively short concave portion 58 along a proximal portion 61 (see FIG. 16). The housing 12 includes a topmost or proximal drive shaft opening 24 through which a proximal portion 66 of the rotational drive shaft extends. The housing 12 includes apertures 56 enable cleaning instruments, cleaning solutions, steam, gas and/or radiation to penetrate inside the housing 12 to sterilize all surfaces of the staple instrument 10. The apertures 56 are shown with an ovoid shape but other shapes are envisioned.

The linkage 20 of the staple instrument 10 comprises an articulated linkage that includes first links 30A, 30B connected to the converter coupling 18 and second links 32A, 32B connected to the first links 30A, 30B. The proximal ends of each of the first links 30A, 30B have a yoked configuration and are secured to holes 46A, 46B in wing portions 47A, 47B of the converter coupling 18 (see FIG. 11) with pins 34A, 34C respectively, in a manner such that the first links 30A, 30B can pivot about the pins 34A, 34C. The staple instrument 10 is further provided with a shaft 36, a boss 38 with an internally threaded bore, and a threaded fastener 40, these components extending through holes 35A, 35B in the second links 32A, 32B and anchor holes 52 in the housing 12 (see FIG. 16) for securing the linkage 20 within a yoke portion 26 of the housing 12 in a manner that permits the second links to pivot about the boss 38 and/or the shaft 36.

The second links 32A, 32B terminate in the jaws 21, 23 of the staple holder 22 which can comprise staple hooks of various sizes and which include staple-engaging offset portions sized to accommodate a particular size or size range of staples. Returning to FIGS. 4 and 5, the jaws 21, 23 each have generally level portions 25A, 25B to enable proper orientation of the staple.

Figure 1:
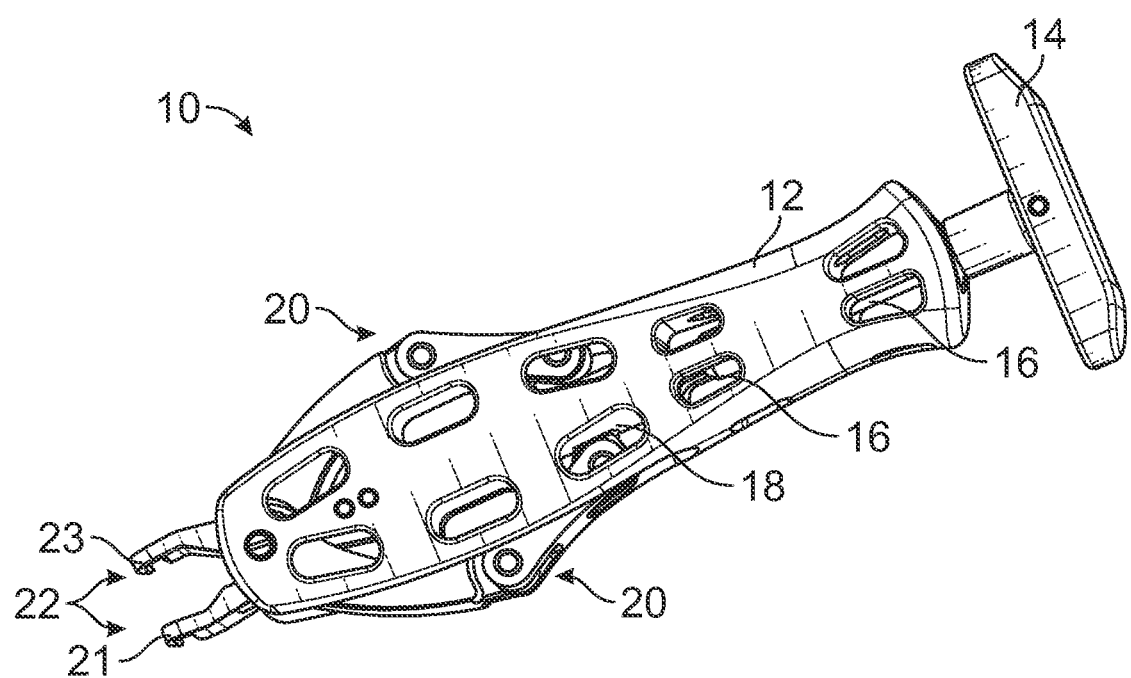
FIG. 1 is an isometric view of an exemplary staple instrument in accordance with the present disclosure.
Figure 2:
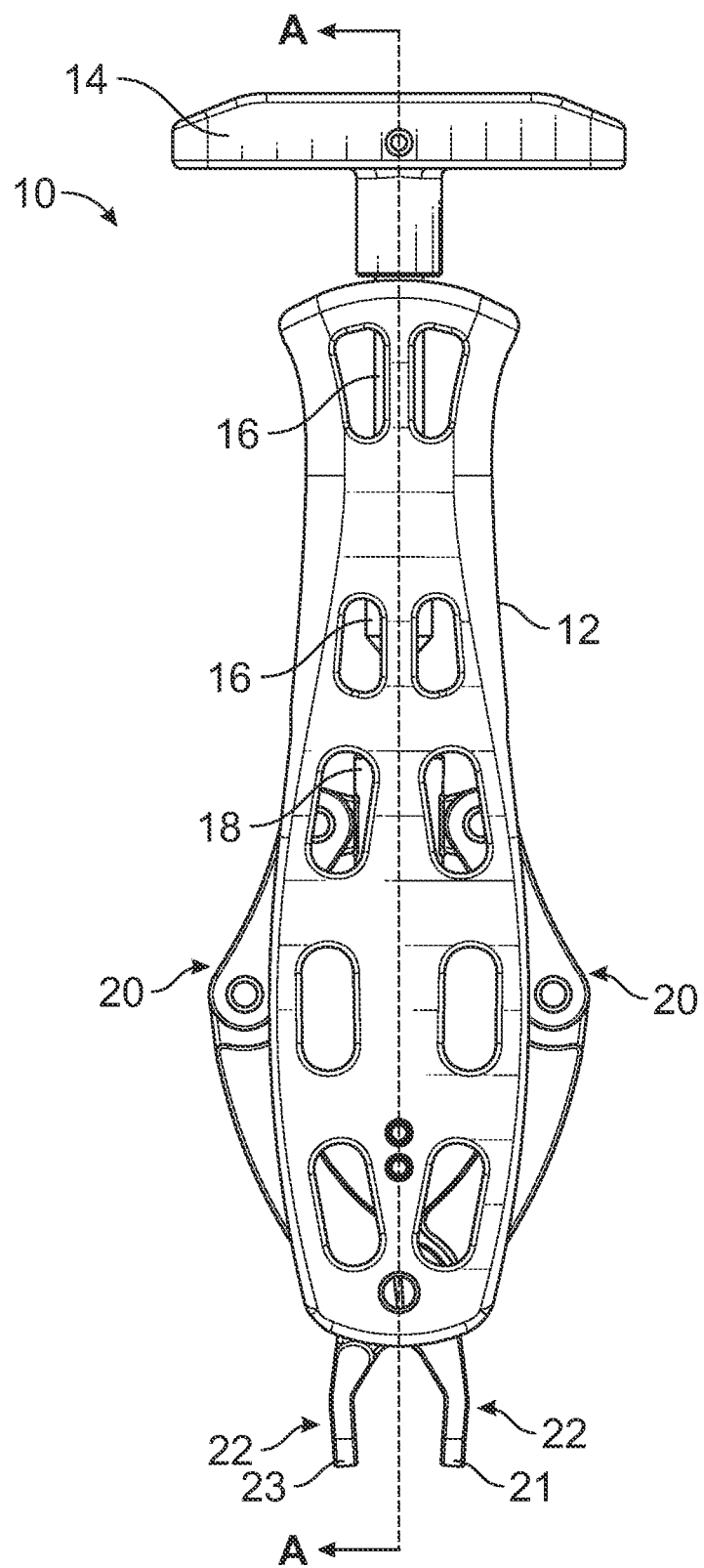
FIG. 2 is a front elevation of the staple instrument of FIG. 1.
Figure 3:
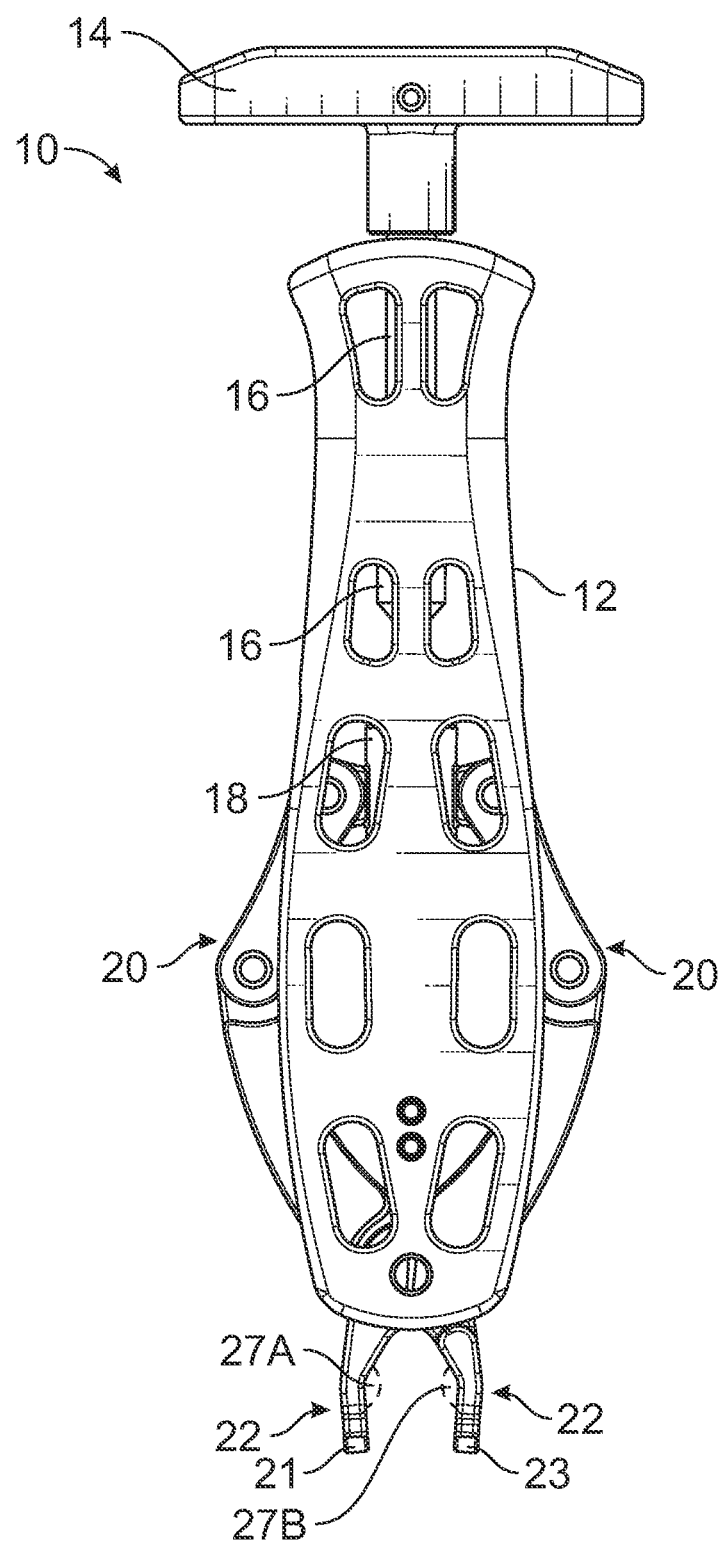
FIG. 3 is a rear elevation of a staple instrument of FIG. 1.
Figure 4:
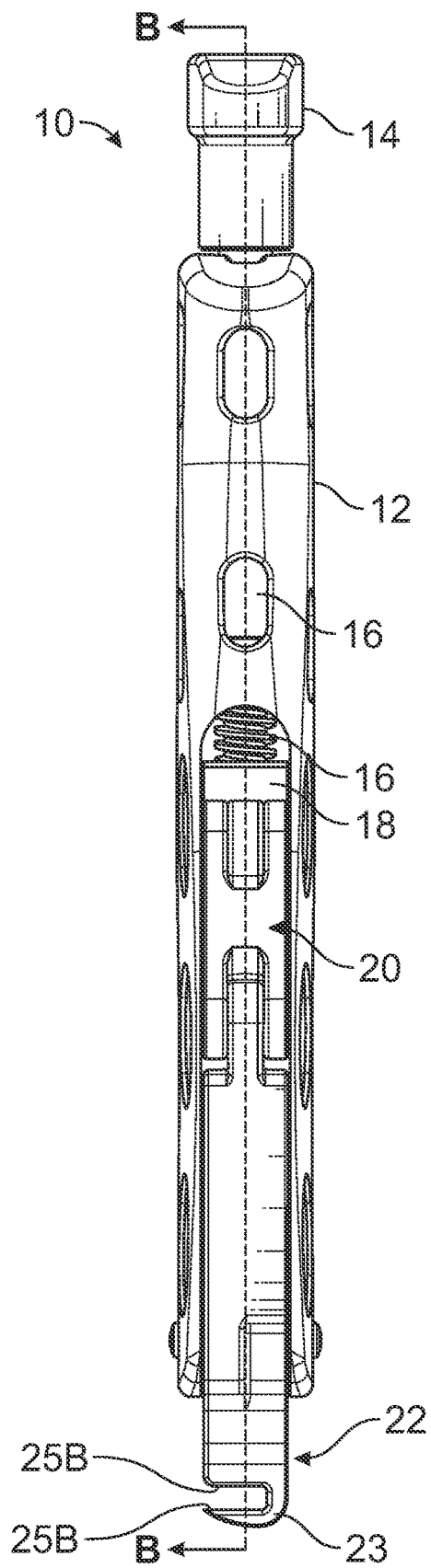
FIG. 4 is a left side elevation of the staple instrument of FIG. 1.
Figure 5:
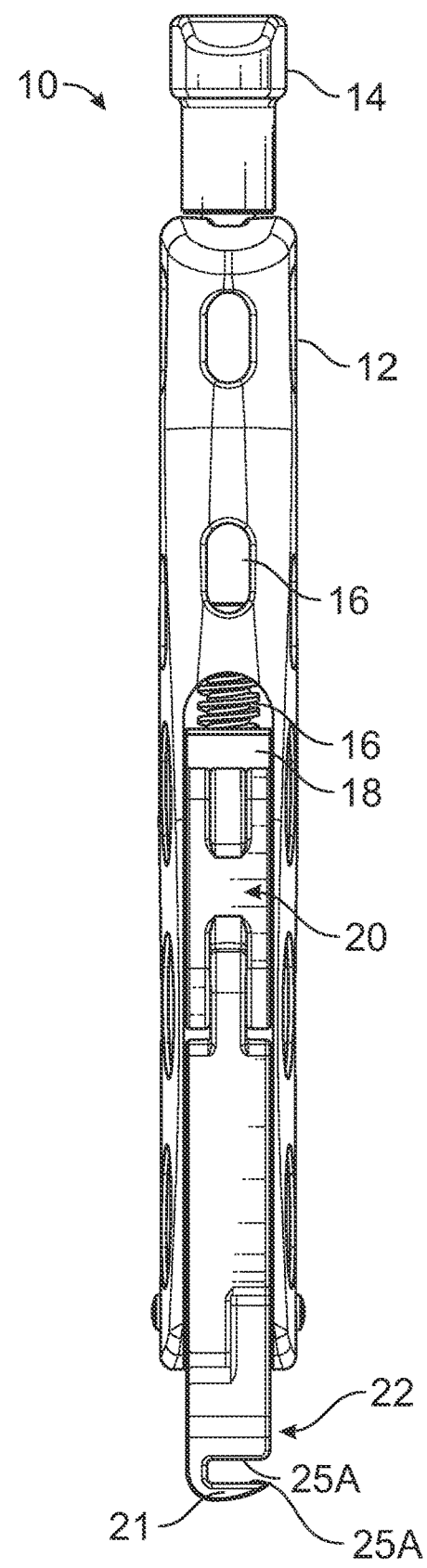
FIG. 5 is a right side elevation of the staple instrument of FIG. 1.

As seen in FIG. 3, the jaws 21, 23 can be positioned at offset angles 27A and 27B respectively. An example offset angle may be 145 degrees, which has been found to work effectively with staples having a bridge length ranging from 15-25 millimeters and a leg length ranging from 15-20 millimeters. Staples for use with the staple instrument 10 may include 15×15, 15×18, 18×18, 18×20, 20×20, and 25×20, where the first number represents the length of the bridge in millimeters, and the second number represents the length of the legs in millimeters. The offset angles 27A, 27B can be reduced for larger staples and increased for smaller staples. In other embodiments not illustrated, the length of the level portions 25A, 25B of the staple jaws 21, 23 can be increased or decreased depending on the size of the staples. Further, the staple instrument 10 itself can be scaled down in size to accommodate smaller staples or scaled up in size to accommodate larger staples.

Figure 10:
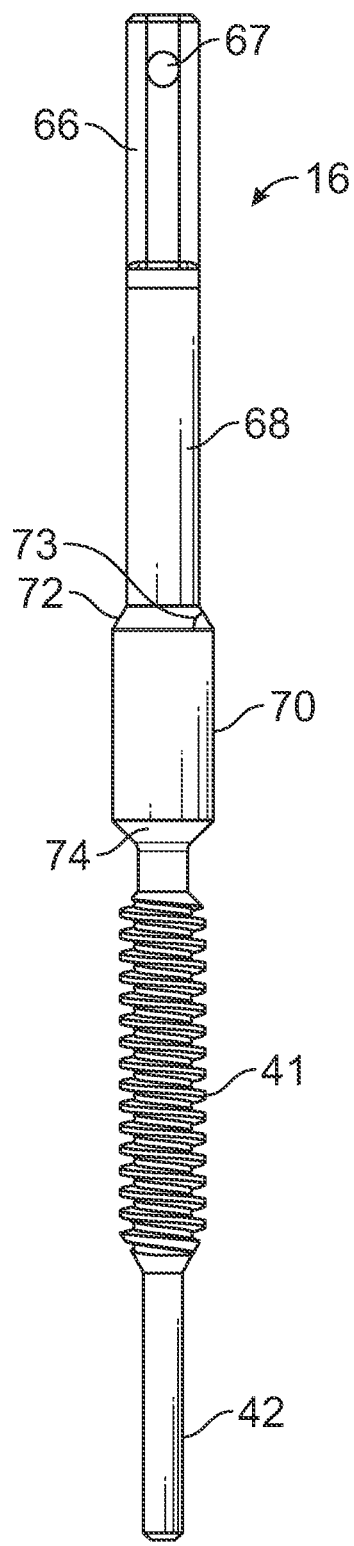
FIG. 10 is a front elevation of the rotational drive shaft of the staple instrument of FIG. 1.

The proximal portion 66 of the rotational drive shaft 16 exits the drive shaft opening 24 of the housing 12, and a handle 14 is attached to the proximal portion 66 of the rotational drive shaft 16 via a pin 34E extending through aperture 67 in the proximal portion 66 (see FIG. 10). Alternative embodiments where the aperture 67 is omitted and/or the pin 34E is replaced with a set screw or other connection mechanism are also contemplated.

Figure 9:
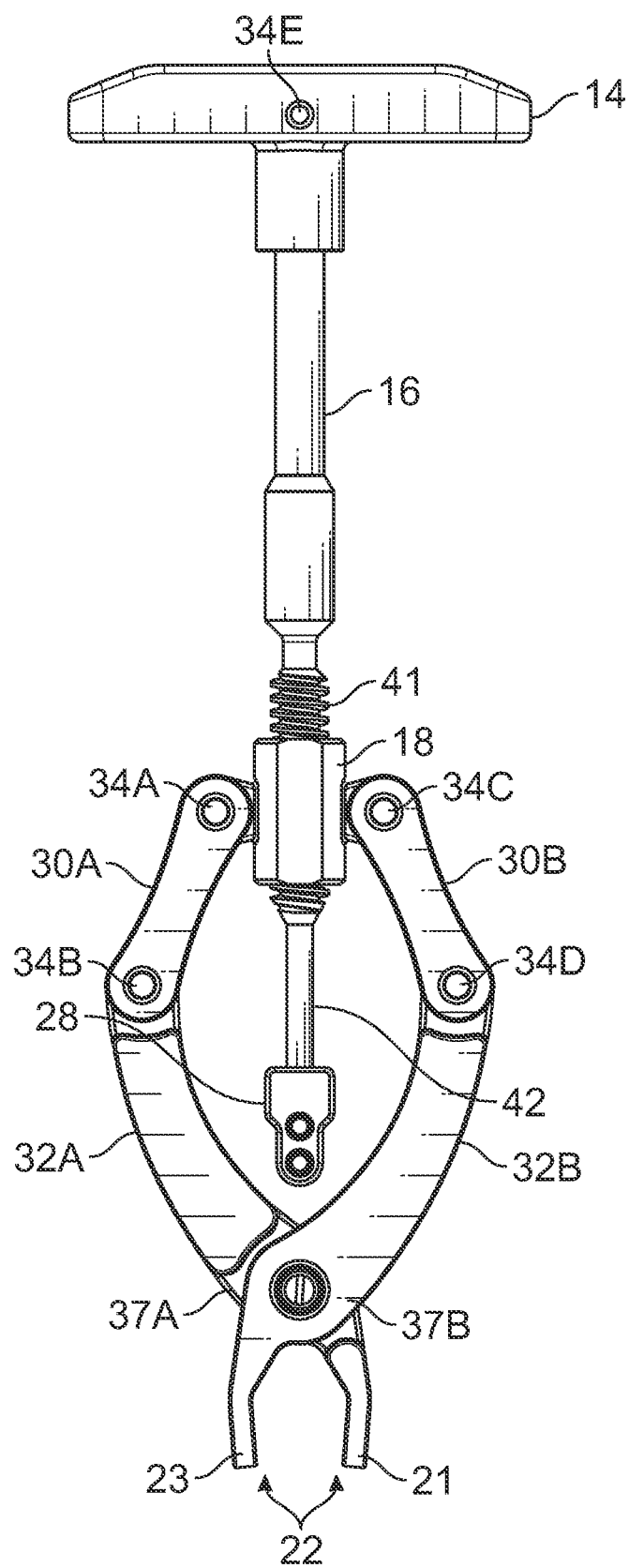
FIG. 9 is a front elevation of the staple instrument of FIG. 1 with the housing removed.
Figure 11:
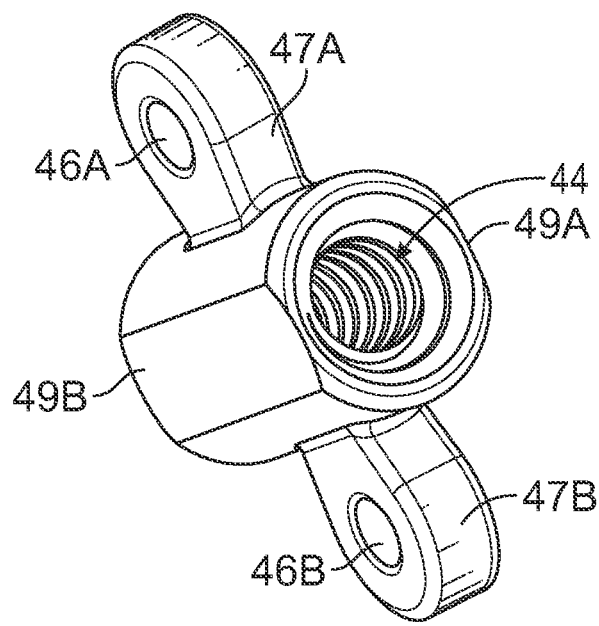
FIG. 11 is an isometric view of the converter coupling of the staple instrument of FIG. 1.

As seen in FIGS. 9 and 10, the rotational drive shaft 16 includes a threaded portion 41 and a distal portion 42. The threaded portion 41 engages an internally threaded bore 44 of the converter coupling 18, as seen in FIG. 11. Rotation of the threaded portion 41 linearly translates the converter coupling 18 relative to the rotational drive shaft 16 when the rotational drive shaft 16 is rotated, in the manner of a screw drive. As shown, the threaded portion 41 can include ¼ inch "ACME" thread. The ¼ "ACME" thread is a robust thread configuration that helps to prevent galling and is more tolerant of debris/fouling when compared with smaller and less robust thread sizes. As illustrated, the threaded portion 41 and the internally threaded bore 44 have a single thread, but a multi-threaded configuration is also possible. It will be appreciated that the threaded drive structure enables very precise adjustments of the jaws 21, 23 to many different intermediate positions.

With further reference to FIG. 10, the rotational drive shaft 16 is a monolithic structure that further includes the proximal portion 66, an intermediate section 68, and a radially more extensive section 70 terminating at a proximal the stop surface 72. Section 70 further includes a distal chamfered surface 74. The stop surface 72 can comprise a beveled or chamfered surface. In the illustrated embodiment, the bevel or chamfer has an angle 73 of approximately 30 degrees, but other configurations also contemplated.

Figure 12:
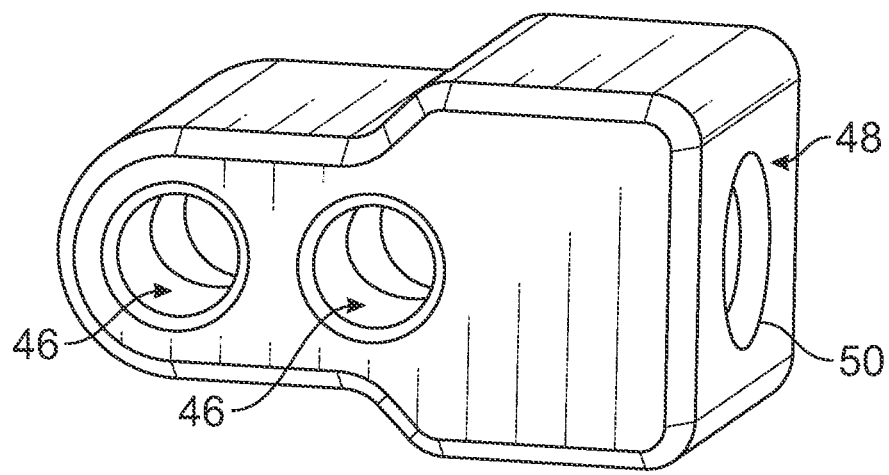
FIG. 12 is an isometric view of the support block of the staple instrument of FIG. 1.
Figure 13:
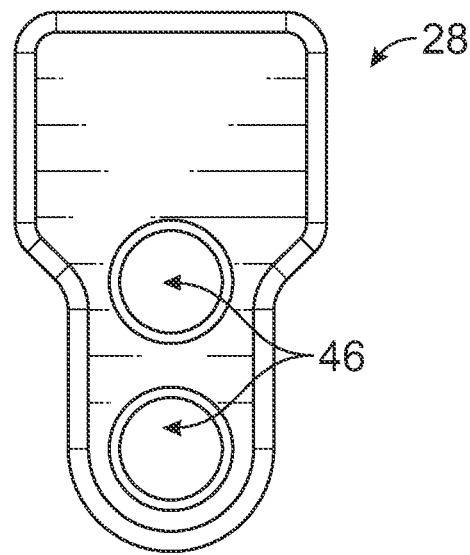
FIG. 13 is a front elevation of the support block of FIG. 12.
Figure 14:
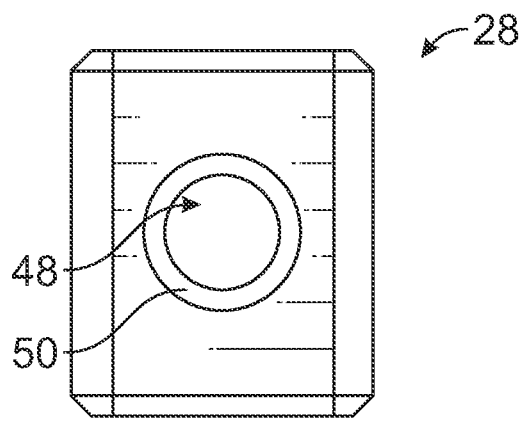
FIG. 14 is a bottom plan of the support block of FIG. 12.
Figure 15:
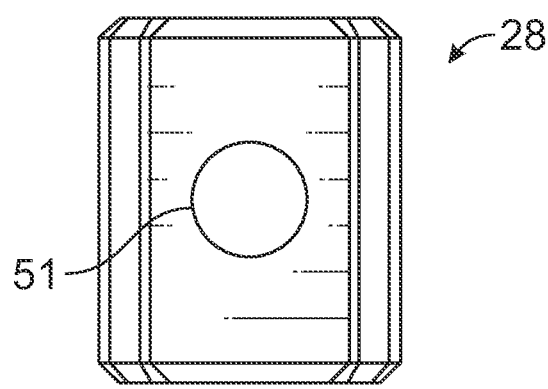
FIG. 15 is a top plan of the support block of FIG. 12.

The staple instrument 10 further includes a support block 28. This component receives an end of the distal portion 42 of the rotational drive shaft 16, and includes a proximal aperture 50, a distal aperture 51, and a bearing 48 (see FIGS. 12 and 15), the bearing 48 configured to receive the distal portion 42 of the rotational drive shaft 16, whereby the distal portion 42 functions as a journal. Because the support block is attached to the housing 12 via pins 34F, 34G through anchor holes 54 in the housing 12 (see FIG. 8), the support block maintains the radial position of the rotational drive shaft 16 with respect to the housing 12 during operation.

The converter coupling 18 includes a pair of opposing lobes or wings 47A, 47B that are provided with holes for use in attachment to the linkage 20 as heretofore described. The converter coupling 18 also includes opposing flats 49A, 49B that engage interior flat surfaces 55A, 55B (shown in FIG. 20) of the housing 12 to guide reciprocating movement of the converter coupling 18 during operation of the staple instrument 10. The engaging flats also prevent rotation of converter coupling 18 relative to the housing 12 during operation.

Figure 18:
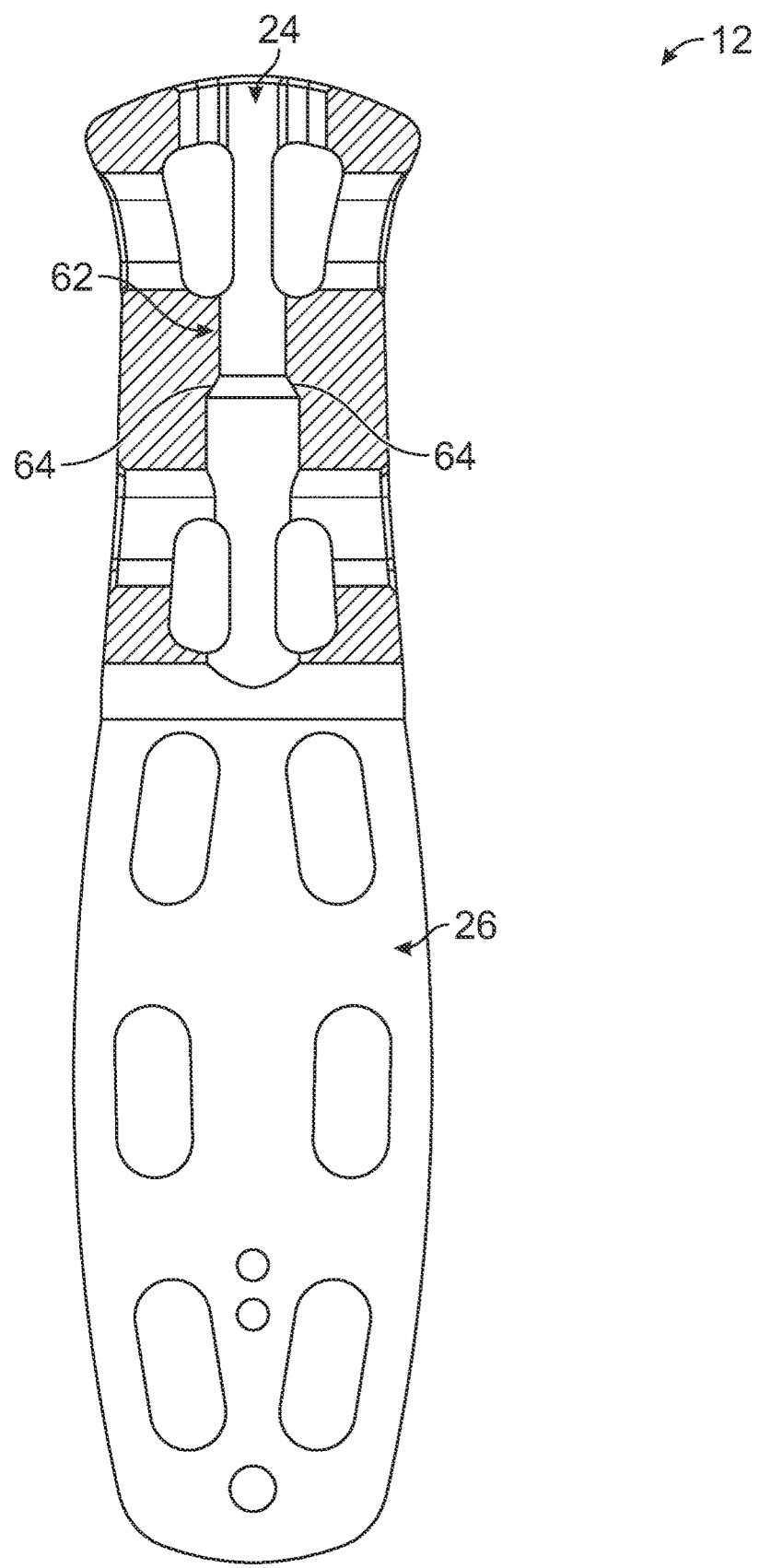
FIG. 18 is a cross-section of the housing of FIG. 16 taken along the line C-C in FIG. 17.
Figure 19:
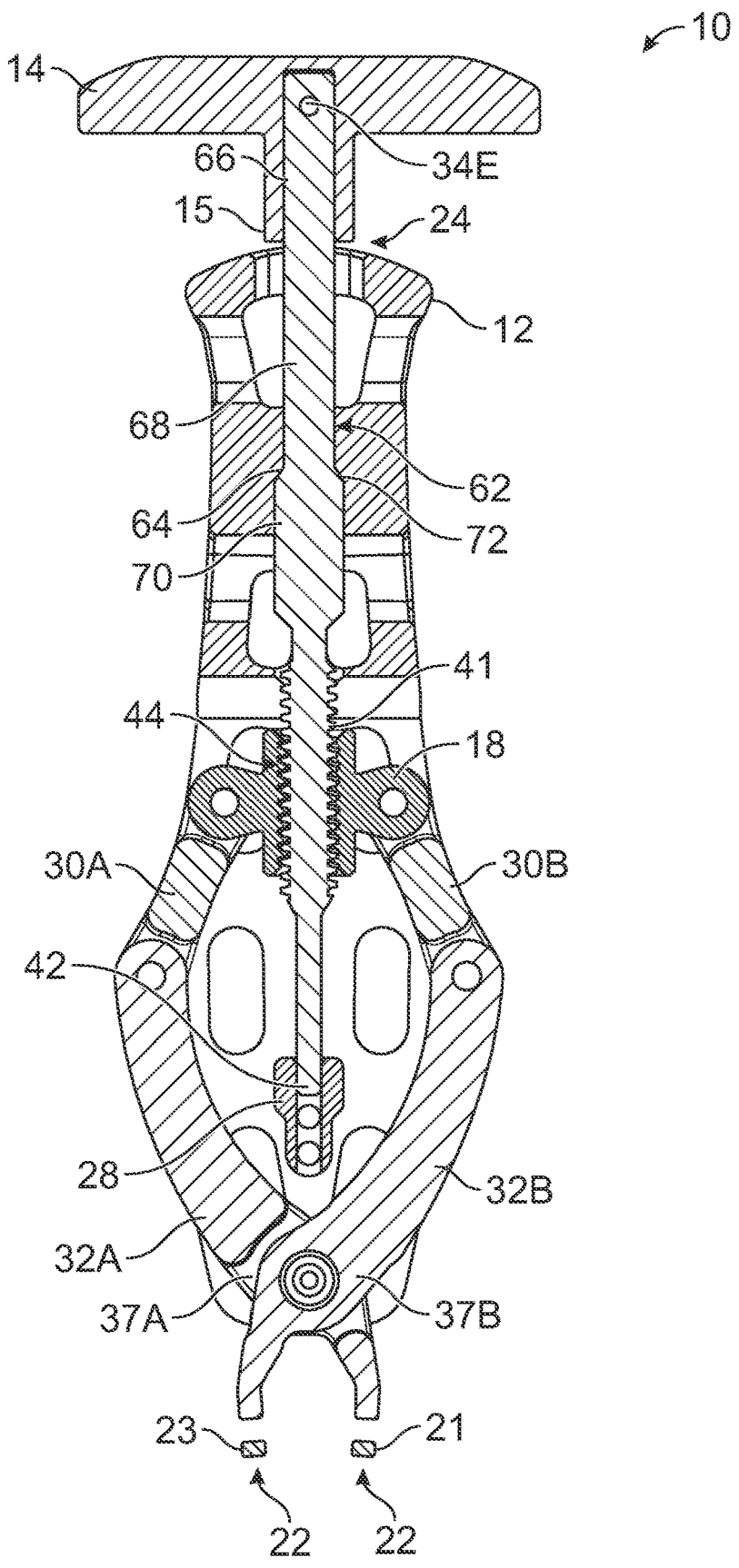
FIG. 19 is a cross-section of the staple instrument taken along line B-B in FIG. 4.
Figure 20:
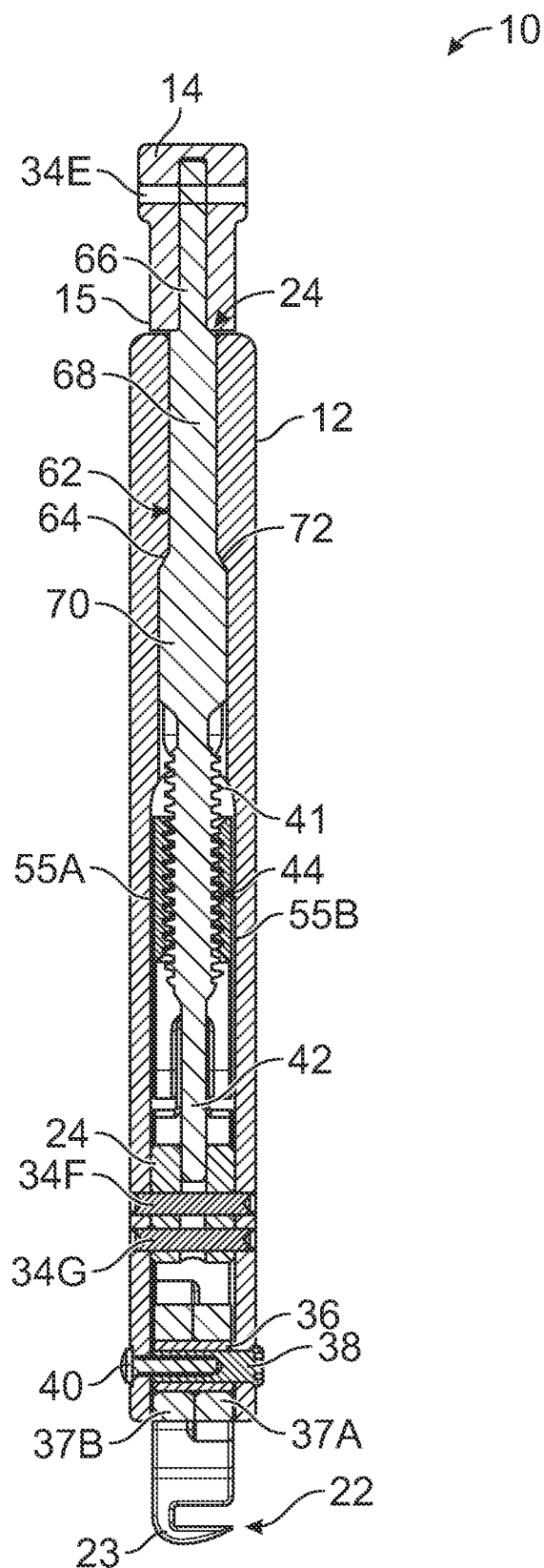
FIG. 20 is a cross-section of the staple instrument taken along line C-C in FIG. 2.

As seen in FIG. 18, the housing 12 includes an axial passage 62 that extends from a top of the yoke portion 26 to the drive shaft opening 24. Further, the axial passage 62 includes a surface 64 configured to engage a stop surface 72 of the rotational drive shaft 16. As illustrated, the housing 12 is monolithic in construction and the axial passage is monolithically formed in the housing, and the surface 64 is configured as a chamfered region sized to receive the beveled stop surface 72 of the rotational drive shaft 16 to inhibit proximal translation of the rotational drive shaft 16 relative to the housing 12 when the staple instrument 10 is operated. Preferably, the stop surface 72 mirrors the shape of the surface 64 so that there is a large area of face-to-face contact therebetween when the shaft is in place. It will be appreciated that other configurations for the surface 64 and the stop surface 72 besides the angled configuration shown in FIGS. 19 and 20 are contemplated. For example, the surface 64 can comprise a substantially flat shelf that interfaces with a similarly flattened variant of the stop surface 72.

As seen in FIGS. 19 and 20, a distal end 15 of the handle 14 is sized relative to drive shaft opening 24 in the housing 12 to occlude distal translation of the rotational drive shaft 16 relative to the housing 12. Upon securement of the handle 14 to the proximal portion 66 of the rotational drive shaft 16, the rotational drive shaft 16 is captured axially within the axial passage 62 of the housing 12, while permitting an operator to rotate the rotational drive shaft 16 using the handle 14. The handle 14 has a proximal end having a generally flat profile (seen especially in FIGS. 7 and 20) that can serve as a biasing surface to allow tapping or other application of an insertion force to the staple instrument 10 to assist in inserting a staple into a bone.

Upon assembly, the pins 34A-G are permanently affixed to the housing via laser welding or the like. The various apertures may be sized to permit the pins to be countersunk.

To operate the device, a user rotates the handle 14 to cause rotation of the rotational drive shaft 16. Via the threaded engagement with the converter coupling 18, the rotational motion of the rotational drive shaft 16 drives the converter coupling 18 axially forward (i.e., distally toward the staple holder 22) to translate the converter coupling 18 relative to the rotational drive shaft 16. As the converter coupling 18 translates distally, the first links 30A, 30B pivot about the pins 34A, 34C at the converter coupling 18 and drive the proximal portions of the second links 32A, 32B outward, pivoting about the pins 34B, 34D that couple the second links 32A, 32B to the first links 30A, 30B and cause the distal portions 37A, 37B of the second links 32A, 32B to pivot about the boss 38 and/or the shaft 36. This action separates the staple jaws 21, 23 of the staple holder 22, to thereby impart a biasing force on a staple (not shown in FIGS. 19 and 20) loaded onto the jaws 21, 23.

Figure 21:
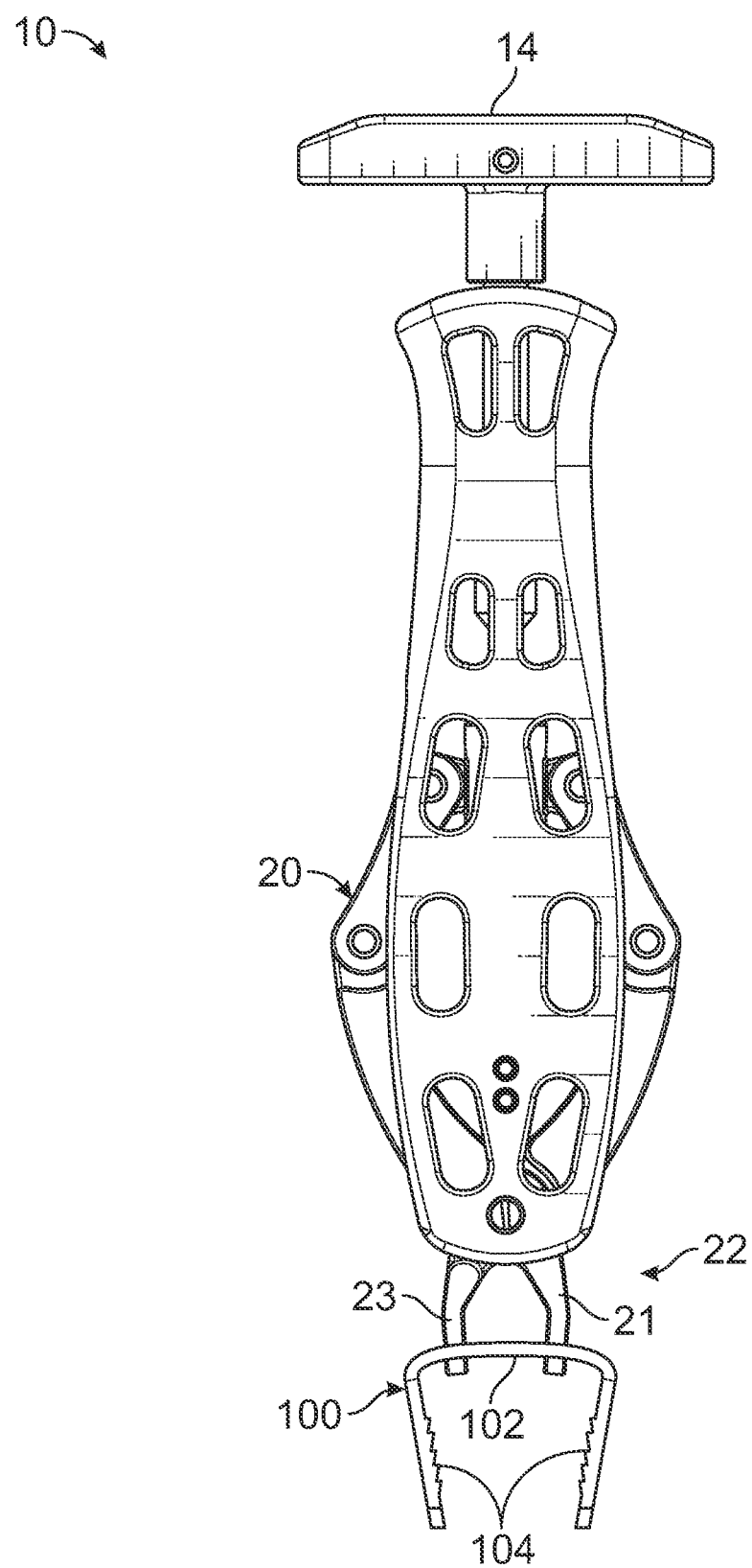
FIG. 21 is a is a front elevation of the staple instrument of FIG. 1 and a loaded staple, the staple coupling of the staple instrument in an expanded position relative to the position of the staple coupling in FIG. 22.
Figure 22:
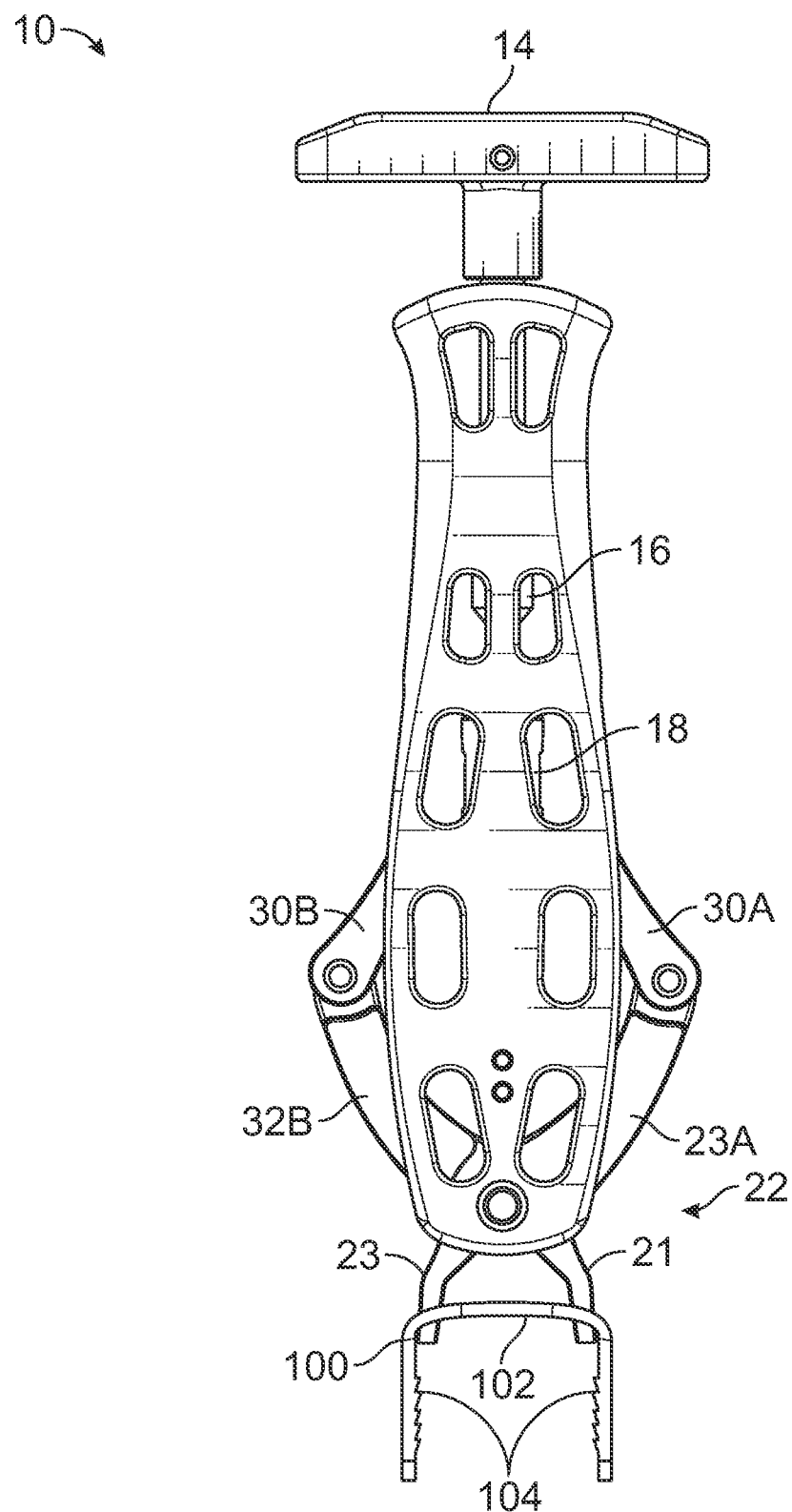
FIG. 22 is a front elevation of the staple instrument of FIG. 1 in a staple loading position.

With reference to FIGS. 21 and 22, a staple 100 in its resting configuration is loaded onto the jaws 21, 23 of the staple instrument 10. A bridge 102 of the surgical staple 100 is first inserted into the staple holder 22 such that legs 104 of the surgical staple 100 extend away from the staple holder 22. As seen in FIG. 21, the legs 104 of the surgical staple 100 are angled inward towards each other when in the resting configuration. A user turns the handle 14, which, via the mechanism described hereinabove, causes the jaws 21, 23 to separate to thereby splay the legs 104 from their initial inward directed position to the open configuration where they are parallel or nearly parallel with one another. In this position, the legs 104 can be inserted into holes into the bone 200 as seen in FIG. 23. The superelastic metal construction of the staple induces the surgical staple to return to the resting configuration. In this way, the legs of the surgical staple can act to compress or hold portions of the bone 200 together.

After the surgical staple 100 is inserted into the bone 200, the rotational drive shaft 16 may be rotated in a second direction opposite the first direction to contract the staple holder 22 to release tension and to assist in removing the surgical staple 100 therefrom. In some embodiments, the first direction is clockwise from the vantage point of the user and the second direction is counterclockwise, but the inverse is also contemplated with differently handed threading.

It has been found that superelastic staples, particularly relatively small staples, require considerable force to splay open the legs thereof. This can cause stress on the jaws 21, 23 and in turn can generate pressures within the device at the proximal end of the rotational drive shaft 16. The staple instrument 10 is configured to accommodate this stress by the large threaded engagement between the converted coupling and shaft, and by the large area of engagement between the beveled stop surface 72 and the surface 64 within the housing 12. This large area reduces the internal pressures generated within the housing 12 as compared to those generated within the device shown in application Ser. No. 17/322,580.

Figure 24:
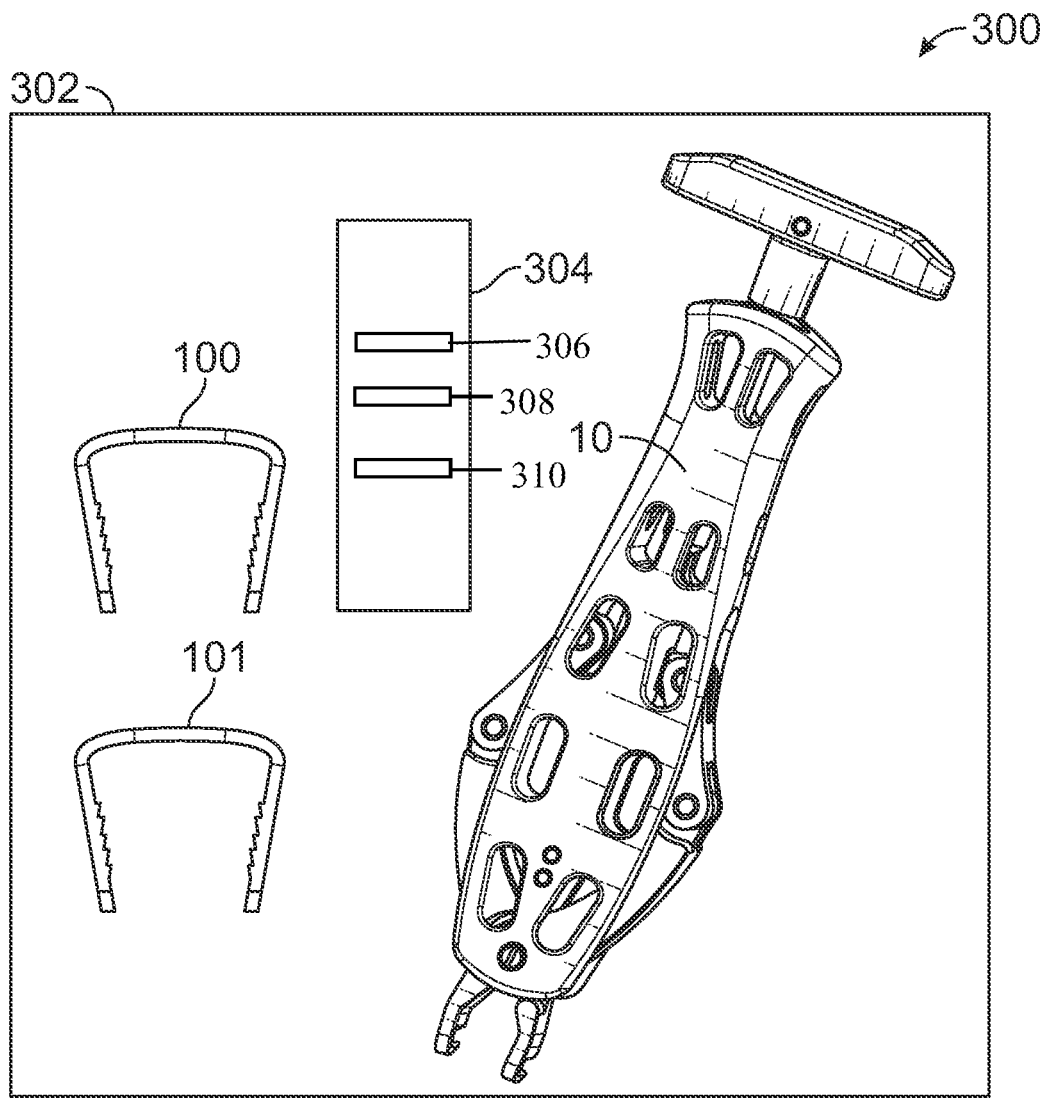
FIG. 24 is a schematic representation of a kit that includes the staple instrument of FIG. 1 and two staples in a container.

As seen in FIG. 24, a kit 300 comprises the staple instrument 10 and one or more staples, which in the illustrated embodiment comprise surgical staples 100, 101 (not to scale in FIG. 24) each made of a nitinol alloy. These components are housed in a container 302 configured to hold the one or more staples and the staple instrument 10. The kit 300 can also include one or more accessory instruments 304. The one or more accessory instruments 304 can include one or more of at least one of a drill guide 306, at least one drill bit 308, pins 310, and a tamp, and in practice can include many other components for use in carrying out the various surgical procedures described herein.

The kit 300 can be used as a unit in conjunction with various surgical procedures that involve insertion or removal of staples from a bone. For example, in typical use a surgeon first selects the most appropriate size staple and drill guide from the kit 300 for a particular patient's anatomy. The selected staple is loaded onto the staple instrument 10 and manipulated into the open configuration as described herein. Then, the drill guide is placed against the bone and the drill bit is used to drill through drill sleeve to drill pilot holes for the selected staple. The staple then is inserted into the bone. If desired, the tamp and a mallet can be used to seat the bridge of the staple flush with the bone after the staple instrument 10 is removed and placement of the staple is verified visually or with instrumentation. If the staple requires repositioning or removal, the staple instrument 10 can be used to pry, expand and lift the staple from its seated position.

It is thus seen that a staple instrument is provided, as are kits and surgical methods. Although described principally in connection with insertion of a staple, it will be appreciated that the staple instrument 10 can be used to assist in removal of a surgical staple from a bone.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention.

No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A staple instrument comprising:
 a staple holder;
 a rotational drive shaft;
 a linkage operatively coupled to the staple holder and configured to expand the staple holder via an expansion motion imparted thereon;
 a converter coupling intermediate the rotational drive shaft and the linkage, the converter coupling configured to convert rotational motion of the rotational drive shaft into the expansion motion of the staple holder; and
 a housing that supports the linkage, converter coupling, and rotational drive shaft;
 the rotational drive shaft having a stop surface engaging a corresponding surface formed in the housing to inhibit proximal translation of the rotational drive shaft relative to the housing.

2. The staple instrument of claim 1, further comprising an axial passage monolithically formed in the housing, the axial passage including the corresponding surface of the housing.

3. The staple instrument of claim 1, wherein the stop surface comprises a beveled surface of the rotational drive shaft and the corresponding surface in the housing comprising an interior chamfer shaped to engage said beveled surface.

4. The staple instrument of claim 1 further comprising a support block coupled to the housing and having a bearing sized to receive a distal journal portion of the rotational drive shaft to maintain a radial position of the rotational drive shaft with respect to the housing, the converter coupling, and the support block.

5. The staple instrument of claim 4, further comprising one or more pins that couple the support block to the housing.

6. The staple instrument of claim 1, wherein a proximal end of the rotational drive shaft terminates in a handle.

7. The staple instrument of claim 6, wherein the rotational drive shaft exits the housing at an aperture, wherein a dimension of a distal end of the handle is sized relative to the aperture to occlude distal translation of the rotational drive shaft relative to the housing.

8. The staple instrument of claim 7, wherein the handle includes a proximal end having a generally flat profile.

9. The staple instrument of claim 1, wherein the rotational drive shaft includes a threaded portion sized to engage a threaded bore of the converter coupling such that rotation of the threaded portion of the rotational drive shaft linearly translates the converter coupling relative to the rotational drive shaft, and wherein the linear translation of the converter coupling effectuates the expansion motion of the staple holder via the linkage.

10. The staple instrument of claim 9, the linkage comprising an articulated linkage.

11. The staple instrument of claim 1, wherein the rotational drive shaft is rotatable in a first direction and a second direction, the first direction being rotational motion that is converted into the expansion motion of the staple holder and the second direction being rotational motion that is converted into a contractive motion of the staple holder.

12. A kit comprising:
 one or more staples; and
 a staple instrument, the staple instrument comprising:
  a staple holder configured to interface with the one or more staples;
  a rotational drive shaft;
  a linkage operatively coupled to the staple holder and configured to expand the staple holder via an expansion motion imparted thereon, the expansion motion configured to transition the one or more staples from a resting configuration into an open configuration;
  a converter coupling intermediate the rotational drive shaft and the linkage, the converter coupling configured to convert rotational motion of the rotational drive shaft into the expansion motion of the staple holder; and
  a housing that supports the linkage, converter coupling, and rotational drive shaft;
  the rotational drive shaft having a stop surface engaging a corresponding surface formed in the housing to inhibit proximal translation of the rotational drive shaft relative to the housing.

13. The kit of claim 12 further comprising a container configured to hold the one or more staples and the staple instrument.

14. The kit of claim 12 wherein the one or more staples are formed from a superelastic metal material, and wherein the superelastic metal material induces the one or more staples to return to the resting configuration after being transitioned into the open configuration by the staple instrument.

15. The kit of claim 12, wherein the rotational drive shaft includes a threaded portion sized to engage a threaded bore of the converter coupling such that rotation of the threaded portion of the rotational drive shaft linearly translates the converter coupling relative to the rotational drive shaft, and wherein the linear translation of the converter coupling effectuates the expansion motion of the staple holder via the linkage.

16. The kit of claim 12, wherein the rotational drive shaft is rotatable in a first direction and a second direction, the first direction being rotational motion that is converted into the expansion motion of the staple holder and the second direction being rotational motion that is converted into a contractive motion of the staple holder.

17. The kit of claim 12, wherein the staple instrument further comprises a support block coupled to the housing and having a bearing sized to receive a distal journal portion of the rotational drive shaft to maintain a radial position of the rotational drive shaft with respect to the housing, the converter coupling, and the support block.

18. The kit of claim 12, further comprising one or more accessory instruments, the one or more accessory instruments including one or more of a drill guide, a drill bit, and locator pins.

19. A method for inserting a staple comprising:
 providing a staple instrument, the staple instrument comprising:
  a staple holder;
  a rotational drive shaft having a stop surface;
  a linkage operatively coupled to the staple holder;
  a converter coupling intermediate the rotational drive shaft and the linkage; and a housing that supports the linkage, converter coupling, and rotational drive shaft, the housing having a surface which corresponds to the stop surface of the rotational drive shaft;

loading a staple into the staple holder;

rotating the rotational drive shaft in a first direction to transition the staple from a resting configuration to an open configuration via an expansion motion.

20. The method of claim 19 further comprising:

inserting legs of the staple into bone material; and releasing the staple from the staple instrument.

\* \* \* \* \*